United States Patent [19]

Zucker et al.

[11] 4,376,079
[45] Mar. 8, 1983

[54] PROCESS FOR THE CONTINUOUS PRODUCTION OF WATER INSOLUBLE METAL SOAPS

[75] Inventors: Friedrich J. Zucker; Georg Osthaus, both of Neuss; Gernot Hänig, Bad Harzburg; Karl Culemeyer, Pinneberg, all of Fed. Rep. of Germany

[73] Assignee: Supraton F. J. Zucker GmbH, Neuss, Fed. Rep. of Germany

[21] Appl. No.: 258,511

[22] Filed: Apr. 28, 1981

[30] Foreign Application Priority Data

May 3, 1980 [DE] Fed. Rep. of Germany ....... 3017121

[51] Int. Cl.$^3$ .......................... C11B 3/06; C08H 17/36
[52] U.S. Cl. .................................... 260/413; 260/414; 260/417; 252/369
[58] Field of Search .................... 260/413 S, 414, 417; 252/369

[56] References Cited

U.S. PATENT DOCUMENTS

| | | | |
|---|---|---|---|
| 2,650,932 | 9/1953 | Kebrich | 260/413 S |
| 4,240,972 | 12/1980 | Mag et al. | 260/424 |
| 4,276,227 | 6/1981 | Kirby | 260/425 |
| 4,307,027 | 12/1981 | Borzelli et al. | 260/414 |

Primary Examiner—John F. Niebling
Attorney, Agent, or Firm—Merriam, Marshall & Bicknell

[57] ABSTRACT

A process for producing a water insoluble metal soap comprising:

A. producing an aqueous dispersion of a basic metal carbonate by adding a metal oxide or hydroxide to water and then simultaneously adding aqueous ammonia and gaseous carbon dioxide thereto;

B. producing a saponified aliphatic acid aqueous emulsion by emulsifying a liquid aliphatic acid with water with stirring and simultaneously adding a small amount of aqueous ammonia thereto; and C. reacting the intermediate products from steps A and B to produce the desired aliphatic acid metal soap by combining the said intermediate products under high shearing conditions.

11 Claims, No Drawings

PROCESS FOR THE CONTINUOUS PRODUCTION OF WATER INSOLUBLE METAL SOAPS

This invention relates to the production of metal soaps. More particularly, this invention is concerned with an improved process of producing water insoluble metal salts or soaps of aliphatic acids.

BACKGROUND OF THE INVENTION

It is well known that water insoluble metal soaps, namely salts of metals with saturated aliphatic acids containing three or more carbons, can be produced by various processes. The most important process, presumably, uses a double composition reaction. In this reaction, a previously prepared aqueous solution of an alkali metal or ammonium salt of the aliphatic acid is reacted with a metal salt to produce the desired metal soap. Metal sulfate, chloride, nitrate and acetate salts are representative of the metal salts which can be used in the process. Even though large amounts of metal soaps are still being produced by this process, the process has substantial disadvantages. The main disadvantage is that the metal soaps obtained are generally insufficiently pure primarily because inorganic salts, such as, for example, sodium or ammonium sulfate or chloride, are carried along and trapped in the precipitating metal soaps.

A so-called direct process for producing metal soaps is described in German Pat. No. 860,210. In this process, a dispersion of a metal oxide or metal hydroxide is directly contacted and reacted with an emulsion of the aliphatic acid in water. This process, however, is only useful with metal oxides which are readily, or relatively readily, soluble in water and thus form the corresponding hydroxides. Metals which form water insoluble hydroxides do not react, even when dispersed, with the free aliphatic acids.

It is also known from German published patent application AS No. 11 89 973 to produce a metal soap by first forming an aqueous suspension of an insoluble metal oxide or hydroxide, introducing carbon dioxide into the suspension to form a basic metal carbonate, and then combining this aqueous suspension with a free aliphatic acid aqueous emulsion. The resulting reaction proceeds smoothly to yield the desired metal soap, as for example zinc soap. It is advantageous for the aliphatic acid aqueous emulsion to be saponified with ammonia and also for the suspension of the basic metal carbonate, such as zinc carbonate, to be made ammoniacal. The precipitated metal soap can be filtered off and, without washing, be dried in the usual manner. Whatever residual ammonia is possibly present is removed with the water.

The described direct process has an advantage over the double decomposition process in that an electrolyte-free product is formed in a single processing step. Also, no electrolyte-containing waste water is obtained since no prior step uses an alkali metal hydroxide and, consequently, environmental pollution is avoided. Nevertheless, there are distinct disadvantages with this process. Thus, it is a batch, rather than a continuous process. Furthermore, special filters, for example, chamber filter presses, are required to separate the precipitated metal soap from the water before the soap is dried in a conventional manner, such as in a flowing air, or circulating air, dryer. An improved process which is not limited to batch operation and/or a filtration of the soap, is accordingly needed.

THE INVENTION

According to the present invention there is provided a process of producing a water insoluble metal soap comprising:

A. producing an aqueous dispersion of a basic metal carbonate by adding a metal oxide or hydroxide to water and then simultaneously adding aqueous ammonia and gaseous carbon dioxide thereto;

B. producing a saponified aliphatic acid aqueous emulsion by emulsifying a liquid aliphatic acid with water with stirring and simultaneously adding a small amount of aqueous ammonia thereto; and C. reacting the intermediate products froms steps A and B to produce the desired aliphatic acid metal soap by combining the said intermediate products under high shearing conditions.

The described process will lead to a pasty or semi-dry metal soap depending on the amount of water used.

Although the process is described in terms of steps, that is only for convenience and clarity and it should be understood that the process is intended to be operated continuously.

Some of the metal oxides and hydroxides which can be used in the process are the zinc, calcium, magnesium and lithium oxides and hydroxides.

Aliphatic acids primarily useful in the process are the monocarboxylic acids, especially those having 8 to 22 carbon atoms in a chain such as palmitic acid, caprylic acid and myristic acid.

Step or operation C described above is desirably effected by feeding the intermediate products into the shearing field of a shear machine having a rotor and a stator, such as one in which the rotor and stator have meshing or engaging radial surfaces. Such a machine can also be used advantageously for producing the intermediate product of step A and, if desired, it can also be used to produce the intermediate product of step B. U.S. Pat. No. 3,995,838 discloses a shear machine which can be used in this process.

With regard to step A described above, the basic metal carbonate intermediate is formed in about 10 to 30 minutes.

The reaction of the intermediate products from steps A and B, in step C, is desirably carried out in the presence of about 20 to 50%, and preferably 30 to 45%, by weight of water at a temperature above the melting point of the aliphatic acid used.

The intermediate products from steps A and B can be fed to the shear mixing machine by use of suitable feeding pumps, preferably in stoichiometric amounts, and they can be reacted at a temperature above the melting point of the aliphatic acid.

The high shearing forces developed in the rotor-stator shear machine, especially one with meshing radial surfaces, makes it possible to bring about a very rapid reaction of the two intermediate products in an especially advantageous manner. As a result, the residence time of the reaction mixture in the shear machine can be limited to a few seconds, and preferably to less than two seconds.

Not only does use of the shear machine in step C provide substantial advantages, but additional advantages are obtained by using it in step A. Thus, when the shear machine is used in step A for the reaction of the metal oxide with water and a small amount of aqueous ammonia with the simultaneous introduction of gaseous carbon dioxide, the reaction time can be reduced to about 10 to 30 minutes compared to the hitherto required 1 to 3 hours. Even shorter reaction times are achieved, according to the invention, when especially reactive metal oxides are used.

Another important advantage of the invention is in the saving of water. The previously described prior art processes, whether single or two step, use water in an amount 12 to 40 times larger than the total amount of the other components. In the process of the invention, the entire amount of water used, inclusive of the water formed in the reaction, only amounts to 20 to 50%, preferably 30 to 40%. This makes possible elimination of all filtering and the time which would otherwise be needed for filtering. The reaction product or metal soap, generally containing about 30 to 45% of water, can be received from the shear machine and be dried directly.

The shear machine used in the reaction preferably has a housing which receives a truncated conical rotor with a surface having coaxial rings of increasing diameter which extend into or mesh with recesses between similar rings on the housing interior wall lying opposite the rotor. Machines of this type are commercially available as are other shear machines which can be used in the process.

It is possible for the first time, by use of the described process of the invention, to continuously produce metal soaps from metal oxides or hydroxides and emulsified aliphatic acids and, in so doing, to eliminate or avoid formation of by-products which are environmentally objectionable. Since only small amounts of water are needed in the process to produce the metal soaps, it is unnecessry to use expensive apparatus, especially filtering devices, particularly filter presses. Metal soaps are produced with high purity, free of electrolytes, in extremely short reaction times and high throughput. Specifically, by means of the described process zinc, calcium, magnesium and lithium soaps of aliphatic acids, particularly monocarboxylic acids having 8 to 22 carbon atoms in a chain, are readily produced. Other metal soaps, however, can be similarly produced.

EXAMPLE 130 kg of zinc oxide is dispersed in a rotor-stator shear machine with 16 liters of 25% aqueous ammonia in 480 liters of cold water with simultaneous introduction of gaseous carbon dioxide. Simultaneously, 900 kg of molten stearic acid is emulsified at 80° C. in 180 liters of water and to the emulsion there is added 36 liters of 25% aqueous ammonia. Both dispersions are fed at 80° C. through correspondingly adjusted dosing pumps to a rotor-stator shear machine likewise heated to 80° C., so that stoichiometric amounts are reacted per unit of time.

From the 130 kg of zinc oxide and 900 kg of stearic acid (saponification number=204) there is formed 1000 kg of zinc stearate. The pasty zinc stearate drawn off from the rotor-stator shear machine has a water content of about 45%. It is fed directly to a flowing air dryer in which it is dried to a water content of 0.2%. The end product is a finely granular, extremely pure, electrolyte-free zinc stearate.

What is claimed is:
1. A process of producing a water insoluble metal soap comprising:
   A. producing an aqueous dispersion of a basic metal carbonate by adding a metal oxide or hydroxide to water and then simultaneously adding aqueous ammonia and gaseous carbon dioxide thereto;
   B. producing a saponified aliphatic acid aqueous emulsion by emulsifying a liquid aliphatic acid with water with stirring and simultaneously adding a small amount of aqueous ammonia thereto; and
   C. reacting the intermediate products from steps A and B to produce the desired aliphatic acid metal soap by combining the said intermediate products under high shearing conditions in a sheer machine having a rotor and a stator.

2. A process according to claim 1 in which the rotor and stator have meshing radial rings.

3. A process according to claim 1 in which the aqueous dispersion of a basic metal carbonate is produced by combining the reactants recited in step A under high shearing conditions.

4. A process according to claim 3 in which the high shearing conditions are effected by a shear machine having a rotor and a stator.

5. A process according to claim 1 in which the metal oxide or hydroxide is a zinc, calcium, magnesium or lithium oxide or hydroxide.

6. A process according to claim 1 or 5 in which the aliphatic acid is a monocarboxylic acid having 8 to 22 carbon atoms in a chain.

7. A process according to claim 1 or 4 in which the saponified aliphatic acid aqueous emulsion is produced by combining the reactants recited in step B under high shearing conditions.

8. A process according to claim 7 in which the high shearing conditions are effected by a shear machine having a rotor and a stator.

9. A process according to claim 1 in which the total amount of water used in the reactions of steps A and B is 20 to 50%.

10. A process according to claim 9 in which the water is 30 to 45%.

11. A process according to claim 1 in which the reactions are effected at a temperature above the melting point of the aliphatic acid.

* * * * *